(12) United States Patent　　(10) Patent No.: US 9,033,927 B2
Maan et al.　　(45) Date of Patent: May 19, 2015

(54) SAFETY INTRAVENOUS CANNULAS

(76) Inventors: Manoj Kumar Maan, New Delhi (IN);
Pankaj Kumar Maan, New Delhi (IN)

( * ) Notice: Subject to any disclaimer, the term of this patent is extended or adjusted under 35 U.S.C. 154(b) by 953 days.

(21) Appl. No.: 12/676,988

(22) PCT Filed: Sep. 3, 2008

(86) PCT No.: PCT/IN2008/000560
§ 371 (c)(1),
(2), (4) Date: Sep. 7, 2010

(87) PCT Pub. No.: WO2009/031161
PCT Pub. Date: Mar. 12, 2009

(65) Prior Publication Data
US 2011/0015573 A1　Jan. 20, 2011

(30) Foreign Application Priority Data
Sep. 6, 2007　(WO) ................. PCT/IN2007/000394

(51) Int. Cl.
*A61M 25/06*　　(2006.01)
*A61M 5/32*　　(2006.01)
*A61M 5/00*　　(2006.01)
*A61M 25/00*　　(2006.01)

(52) U.S. Cl.
CPC ....... *A61M 25/0606* (2013.01); *A61M 25/0631* (2013.01); *A61M 25/0693* (2013.01); *A61M 2025/0089* (2013.01)

(58) Field of Classification Search
CPC ..................... A61M 25/0631; A61M 25/0637; A61M 25/0606; A61M 25/06; A61M 5/50; A61M 5/321; A61M 5/3205
USPC .......... 604/110, 111, 164.08, 165.01–165.04, 604/164.01, 164.07–164.09, 164.11, 198
See application file for complete search history.

(56) References Cited

U.S. PATENT DOCUMENTS

| | | | |
|---|---|---|---|
| 4,944,728 A * | 7/1990 | Carrell et al. | 604/164.08 |
| 5,176,650 A | 1/1993 | Haining | |
| 5,562,631 A * | 10/1996 | Bogert | 604/192 |
| 5,573,510 A * | 11/1996 | Isaacson | 604/158 |
| 5,954,698 A * | 9/1999 | Pike | 604/167.03 |
| 6,939,325 B2 * | 9/2005 | Haining | 604/162 |
| 7,014,622 B1 * | 3/2006 | Pressly et al. | 604/110 |
| 7,112,190 B2 * | 9/2006 | Bressler et al. | 604/263 |

(Continued)

FOREIGN PATENT DOCUMENTS

EP　　1 475 124 A1　　11/2004
EP　　1475124 A1 *　11/2004

(Continued)

*Primary Examiner* — Bhisma Mehta
*Assistant Examiner* — Jenna Zhang
(74) *Attorney, Agent, or Firm* — Ladas & Parry LLP

(57) ABSTRACT

A safety intravenous cannula and catheter device is disclosed. The device permits easy insertion of a cannula made of a biocompatible material into the vein with a guide needle and withdrawal of the guide needle into a safety chamber with an in- built locking mechanism with completely prevents removal and/or reuse of the needle. The needle before insertion is protected by a biocompatible sheath which when inserted into the vein and after withdrawal of the needle acts as catheter. Similarly, after withdrawal the needle is locked inside a safety chamber in such a manner that at no time does the user come into contact with the needle or in any danger of accidental injury.

15 Claims, 6 Drawing Sheets

(56) References Cited

U.S. PATENT DOCUMENTS

2004/0243060 A1* 12/2004 Rossi et al. .............. 604/164.08
2007/0060890 A1* 3/2007 Cuppy .................... 604/164.01

FOREIGN PATENT DOCUMENTS

WO 00/02614 A 1/2000
WO 03/066151 A2 8/2003

* cited by examiner

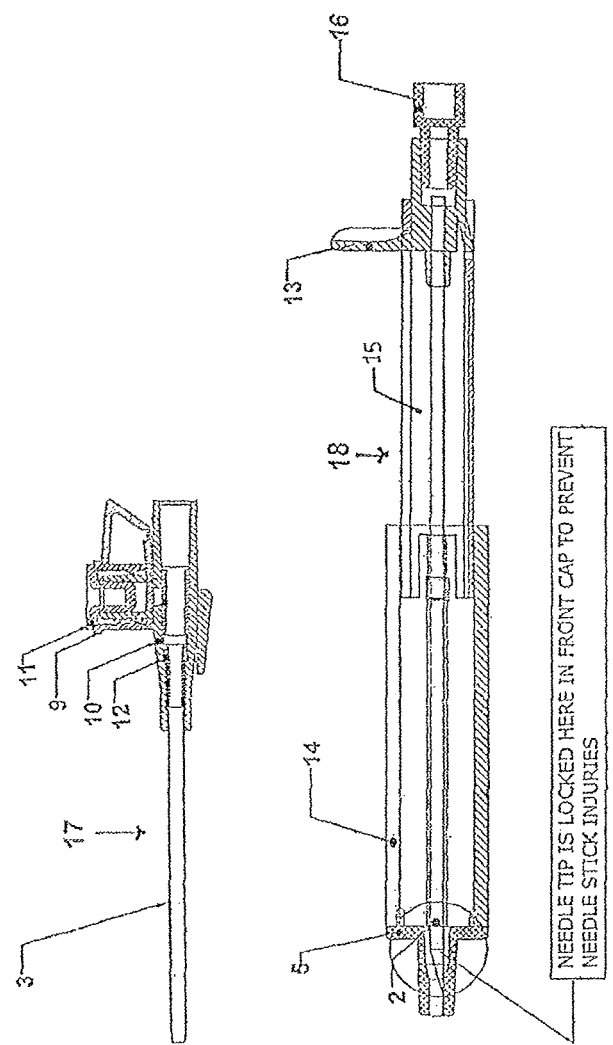

SAFETY INTRAVENOUS CANNULAS

FIELD OF INVENTION

The present invention generally relates to safety intravenous cannulas. In particular, the present invention relates to safety intravenous cannula or catheter insertion devices. More particularly, the present invention relates to disposable intravenous cannula or safety catheter insertion devices comprising needle or cannula and a safety transfer chamber assembly to lock-in and dispose-of used/retracted needle or cannula. More particularly, the present invention relates to cannulation devices with safety features provided therein, which are usable across a wide range of catheters. Specifically, the present invention relates to safety cannula and catheter insertion devices, which eliminate the chances of needle stick injuries to medical and para-medical staff during insertion and while disposal of the used/retracted needle or cannula. The present invention also ensures that at no time does the blood come into contact with the healthcare worker thereby completely eliminating chances of blood borne diseases.

BACKGROUND AND PRIOR ART

The use of clinical devices in which pointed hollow needles or cannulas are employed in order to puncture the skin of a patient, and especially catheters utilizing such needles to effectuate venipunctures, is well known and widely practiced in the medical field for injecting drugs and fluids directly into the bloodstream of patients. Also, during surgery and other surgical procedures, it is often and frequently required that whole blood transfusions and parenteral fluids be administered to the patient undergoing such operations. The introduction of such fluids into the cardiovascular systems of patients has necessitated the forming of a venipuncture utilizing a hollow rigid needle having a proximal attachment site for fluid connection which is adapted to interconnect the needle with a source of intravenously administered fluids.

It is known in the medical art to introduce a thin tubular catheter of a low-friction biocompatible material into the vein of a patient and to permit the catheter tube to remain inserted over lengthier periods of time for purposes of, for example, periodically administering fluids, blood/plasma transfusions, medications in liquid form, collection of blood samples. By this procedure, the trauma, extravasation, and infiltration caused by repeated venipuncture have been largely avoided; it also overcomes the danger and discomfort caused due to leaving a needle inside the body. For the purpose of forming a venipuncture and inserting the catheter tube within the body cavity of a patient, such as a vascular cavaity or vein, the distal end of a flexible catheter tube is guided using a cannula or hollow sharp-tipped needle. Thereafter, the flexible catheter tube, which is slidably coaxially mounted on the outer circumference of the cannula or hollow needle, is advanced along the length of the needle into the vein subsequent to the needle having formed the venipuncture. Following venipuncture, the guide needle is withdrawn from the interior of the catheter tube, while permitting the catheter tube to remain inside the patient body at the site of the venipuncture. Thereafter, the used needle is suitably discarded according to the standard protocols prescribed for disposal.

The needle, which has been previously inserted in the body of the patient during venipuncture may have been exposed to infectious agents. For example, a patient infected with the Acquired Immune Deficiency Syndrome (AIDS) which is frequently or practically always ultimately fatal in nature, or other dangerous infectious conditions such as hepatitis, there is a constant danger or hazard that the clinical personnel or the para-medical staff may accidentally jab or stick themselves with the used needle after withdrawal from the body of the patient, with the possibility of infection or even death resulting therefrom.

Disposable medical devices having piercing elements administering a medicament or withdrawing a fluid require safe and convenient handling both prior to use and after use are known in the art.

For example, WO 2003/045480 relates to a safety needle assembly for injecting a fluid into a human body comprising a cylindrical housing with a bottom surface supporting a needle cannula and a shield telescopically movable relative to the housing. It discloses that a spring located within the housing is used to irreversibly immobilize the safety needle assembly.

U.S. Pat. No. 7,112,190 relates to a safety needle assembly with a needle hub and a needle cannula. It also has wings and describes that wings project transversely from the hub to facilitate manipulation and positioning of the needle assembly. It goes on to describe how a shield assembly is hingedly attached to the needle hub and can be rotated from a first position where the needle cannula is exposed to a second position where the needle cannula is shielded. A latch is also proposed to be disposed on the shield for securing locked engagement with the hub, the wings and/or the tubing extending from the hub. In addition, a spring is also suggested to propel the shield into the second position.

U.S. Pat. No. 7,163,526 discloses a needle assembly having an IV cannula, a non-patient cannula and a flash back chamber at the distal end of the housing. It discloses a shield connected hingably to a portion of the housing proximally of the entrance to the flashback chamber. Post use, the shield is rotated into a closed position to lock the used needle. Hingably connected shield is said to achieve clear visibility of the flashback chamber.

U.S. Pat. No. 7,128,726 discloses a safety shield assembly, which includes a clip with a plurality of cannula finger locks for preventing re-exposure of the used needle.

U.S. Pat. No. 7,041,092 discloses a shield system having a body, shield, spring and ring which provides an interlock of the shield in the retracted position.

Safe handling after use is more important to protect healthcare workers, paramedical staff and the medical personnel involved from needle stick injury. It is, therefore, desirable to shield the used needle cannula immediately after the needle cannula has been withdrawn from the patient. Such shields can prevent any accidental re-exposure of the used needle cannula and preferably, should prevent an intentional attempt to re-use the needle cannula. Such shields have been developed in different forms as described above. For example, some shields telescope in a distal to proximal direction over the needle cannula and frictionally engage the needle hub. However, such shields have risk of accidental needle stick injury if the shield in misaligned with the needle cannula. Other shields are telescoped over the needle hub and can be moved distally over the needle cannula to effect shielding, but such shields can interfere with the normal usage of some medical devices. Some devices employ very short needle cannulas, which are unsuitable if the shields are designed to lock near the distal end of needle cannula. Additionally, a shield designed to lock with a wider gauge needle cannula might be more likely to generate a spray upon engaging a much narrower needle cannula. Furthermore, it may be desirable to reduce the force required to effect shielding without reducing the audible and tactile indications of complete shielding.

Therefore, there exists a need of a safety device, which eliminates the chances of needle stick injuries both during insertion and after insertion and while disposing of the used needle.

OBJECTS OF THE INVENTION

It is therefore, an important object of the present invention to provide a safety device for insertion, withdrawal and safe disposal of a used needle or cannula from the site of its use.

It is a further object of the present invention to provide a safety device, which prevents reuse of such needle.

It is another object of the present invention to provide a safety cannulation device, which completely eliminates accidental pricking or injury to the healthcare workers, paramedical or medical staff.

It is another object of the present invention to provide safety intravenous cannulation and catheter insertion devices, which completely eliminate accidental pricking or injury to the paramedical or medical staff.

It is yet another object of the present invention to provide disposable intravenous cannula and catheter insertion devices comprising needle or cannula and a safety transfer chamber assembly to lock-in and dispose-of used/retracted needle or cannula.

It is still a further object of the present invention to provide intravenous safety cannula and catheter insertion devices with safety features provided therein which are usable across a wide range of catheters, needles and syringes.

It is a further object of the present invention to provide intravenous cannula, which is simple to use, easy to dispose of after use and which overcomes the disadvantages of the prior art devices.

SUMMARY OF THE INVENTION

The above and other objects of the present invention are achieved by providing a safety intravenous cannula and catheter device which permits easy insertion of a catheter made of a biocompatible material into the vein with a guide needle or a cannula and withdrawal of the guide needle into a safety chamber with an in-built locking mechanism with completely prevents removal and/reuse of the needle. The needle before insertion is protected by a bio a compatible sheath which when inserted into the vein and after withdrawal of the needle acts as catheter. Similarly, after withdrawal the needle is locked inside a safety chamber in such a manner that at no time does the user or any other person come into contact with the needle or is in any danger of accidental injury.

In its broadest aspects, the safety intravenous cannulation and catheter device comprises a needle assembly consisting of a needle and a catheter body enclosing said needle therewithin. The catheter body has a flashback chamber to provide indication when blood is withdrawn and to ensure that no bubbles enter the vein. The needle of said needle assembly is connected to a hub, which in a preferred embodiment is integral with the safety transfer chamber. The safety transfer chamber comprises of an outer sleeve slidably mounted around an inner sleeve. The needle is connected to or may be integral with said inner sleeve. Where the needle is not integral with the inner sleeve, it is slidably mounted in the inner sleeve. Where it is integral with the inner sleeve, it moves along with the inner sleeve inside the outer sleeve. The needle hub and the inner sleeve are provided with an interlocking mechanism, preferably comprising of interlocking complementary lugs and indentations. In a preferred embodiment, the lugs are on the needle hub while the indentations are on the inner sleeve. In such a case, once the needle is completely withdrawn from within the catheter, the complementary lugs and indentations on the needle hub and inner sleeve lock with each other with a first 'click'. At this position, the needle hub is locked with the inner sleeve thereby completely preventing reinsertion of the needle into catheter. When the needle hub is pulled back further from this position, it pulls the inner sleeve back with it. The inner sleeve may be tubular or semi tubular with a substantially "U" shaped cross section or may simply comprise of a base with two upstanding and opposing columns said columns being two upright sections of a cylindrical tube, axially mounted around the guide needle. The inner sleeve is provided with at least a pair of lugs at one end, which snap fit into complimentary indentations on the outer sleeve in a locking position. In an alternative embodiment, the lugs may be on the outer sleeve in which case, the indentations are on the inner sleeve.

As stated previously, when the needle hub is pulled back in the inner sleeve from within the catheter, the inner sleeve is partially slided back from the outer sleeve to a first position. At this position, the needle hub locks with the inner sleeve with a "click" at a first position, which prevents the needle from being reinserted into the cannula or protective sheath. When the needle hub is pulled back further, it pulls the inner sleeve with it so that the inner sleeve is fully pulled back within the outer sleeve and it locks with said outer sleeve with a further "click" at a second locking position where it completely prevents further axial or rotational movement of the two sleeves with respect to each other. At this position, the needle, which is connected to or is integral with the inner sleeve is fully withdrawn and it is completely and safely retained in the safety transfer chamber with no part thereof being exposed to human contact. At this position, the lugs of the inner sleeve of the needle assembly are in an irreversible locking position with the corresponding indentations of the outer sleeve and since the needle itself is connected to or integral with the inner sleeve, it now lies immobile within the safety transfer chamber and is permanently safe from further use or reuse. Such irreversible withdrawal and locking of the retracted needle within the safety transfer chamber forms an important aspect of the present invention.

Thus, according to the present invention there is provided an intravenous cannula or catheter insertion device which comprises in combination:
a cannula assembly having a catheter detachably attached to a catheter holder at the distal end and at least one attachment site at the proximal end, having a lumen extending from said distal end to said proximal end; a guide needle mounted on a needle hub for positioning the cannula assembly to an operative position, wherein said catheter is slidably coaxially mounted on the outer circumference of the said guide needle wherein the said guide needle is in fluid communication with said lumen; a safety transfer chamber assembly detachably connected to the cannula assembly at said attachment site, wherein the safety transfer chamber assembly consists of an outer sleeve slidably mounted around an inner sleeve, said needle hub being connected to or integral with said inner sleeve, the needle hub and said inner sleeve being equipped with a first complementary interlocking mechanism such that retracting the needle from the catheter locks the needle hub with the inner sleeve in a first locking position thereby preventing forward movement of the needle and reinsertion of thereof in the catheter, further retraction of the needle hub causing the inner sleeve to retract with it in said outer sleeve, said inner and outer sleeves being equipped with a second complementary locking mechanism such that in a fully retracted position of said inner sleeve, the needle is completely enclosed within the safety transfer chamber and said inner sleeve locks with the outer sleeve at a second locking position, thereby preventing further axial or rotational movement of the two sleeves with respect to each other such that reuse of the needle is completely prevented.

In a preferred embodiment, the first locking mechanism comprises at least a pair of lugs at the forward end of the needle hub, which snap fit into complimentary indentations on the inner sleeve.

In a preferred embodiment, the second locking mechanism comprises at least a pair of lugs at one end of the inner sleeve, which snap fit into complimentary indentations on the outer sleeve.

The inner sleeve may preferably be tubular, semi tubular in the form of a tray with U-shaped cross section or may simply comprise of a base with two upstanding and opposing columns, said columns being two upright sections of a cylindrical tube, axially mounted around the guide needle. Such constructions of the inner sleeve provides a springy or biasing force to the inner sleeve which enable it to lock and snap fit with the outer sleeve at its side walls in a second locking position. Preferably, the inner sleeve is provided with at least a pair of lugs at one end, which snap fit into complimentary indentations on the outer sleeve or vice versa.

In a preferred feature, the said cannula assembly has a securable opening extending from its main body, which is closed using a replaceable port cap.

In another preferred feature, the said guide needle is movable to a retracted position via the proximal end of the cannula assembly for removal therefrom and is irreversibly locked inside the said safety transfer chamber assembly.

In another preferred feature, cannula assembly is shielded/covered by a removable/replaceable protective cover.

In another preferred feature, removable/replaceable cover is provided with a threaded stopper holder to hold a threaded stopper (luer lock).

In another preferred feature, the said threaded stopper (luer lock) is used to securely close the attachment site.

The present invention also provides a safety transfer chamber assembly for use with an intravenous cannulation device having a guide needle, for safely locking in said guide needle after use to prevent reuse or contact with a user, said safety transfer chamber assembly comprising a needle hub for holding and slidably retracting said needle; an outer sleeve slidably mounted around an inner sleeve, said needle being connected to or integral with said inner sleeve, the inner and outer sleeves being sleeve being equipped with a complementary locking mechanism such that in the fully retracted position of the inner sleeve, said inner sleeve locks with the outer sleeve and the needle is completely enclosed within the safety transfer chamber.

In yet another embodiment, the present invention provides a cannula assembly for detachable attachment to a catheter holder at the distal end and at least one attachment site at the proximal end, having a lumen extending from said distal end to said proximal end; a guide needle mounted on a needle hub for positioning the cannula assembly to an operative position, wherein the said guide needle is in fluid communication with said lumen; a safety transfer chamber assembly detachably connected to the cannula assembly at the said attachment site, wherein the safety transfer chamber assembly consists of an outer sleeve slidably mounted around an inner sleeve, said needle hub being connected to or integral with said inner sleeve, the needle hub and said inner sleeve being equipped with first complementary interlocking mechanism such that retracting the needle from the catheter locks the needle hub with the inner sleeve in a first locking position thereby preventing forward movement of the needle and reinsertion of thereof in the catheter, further retraction of the needle hub causing the inner sleeve to retract with it in said outer sleeve, said inner and outer sleeves being equipped with a second complementary locking mechanism such that in a fully retracted position of said inner sleeve, the needle is completely enclosed within the safety transfer chamber and said inner sleeve locks with the outer sleeve at a second locking position, thereby preventing further axial or rotational movement of the two sleeves with respect to each other such that reuse of the needle is completely prevented.

Preferably, the guide needle is a hypodermic needle, which in a more preferred embodiment is beveled, back cut ground and siliconised for smooth and painless venipuncture.

Preferably, the catheter body is generally protected by a needle protection cover.

In use, the site of cannulation is cleaned by an aseptic or antiseptic swab. The catheter is inserted into the patient's vein while holding the hub. After insertion of the cannula into the vein, the needle is gently withdrawn by still holding the hub. This leaves the cannula within the vein but the needle is withdrawn. At a partially withdrawn position, the needle hub locks with said inner sleeve with a first "click" in a such a way that further forward movement of the needle within the inner sleeve is prevented and reinsertion of the needle into the cannula is made impossible. Further withdrawal of the needle hub causes withdrawal of the inner sleeve fully within the outer sleeve with a second "click" at which position, the two sleeves are completely locked with each other which completely prevents their axial or rotational movement with respect to each other. At this point, the needle is fully retracted and lies fully enclosed in the safety chamber thereby entirely preventing further use of the needle. The used device can now be safely disposed of without any risk of any injury to any person.

BRIEF DESCRIPTION OF THE ACCOMPANYING DRAWINGS

The present invention will now be described with reference to the accompanying drawings in wherein:

FIG. 6 is a diagrammatic representation of the retracted needle locked in the safety chamber assembly detached from the cannula assembly.

DETAILED DESCRIPTION OF THE INVENTION

Figure 1:
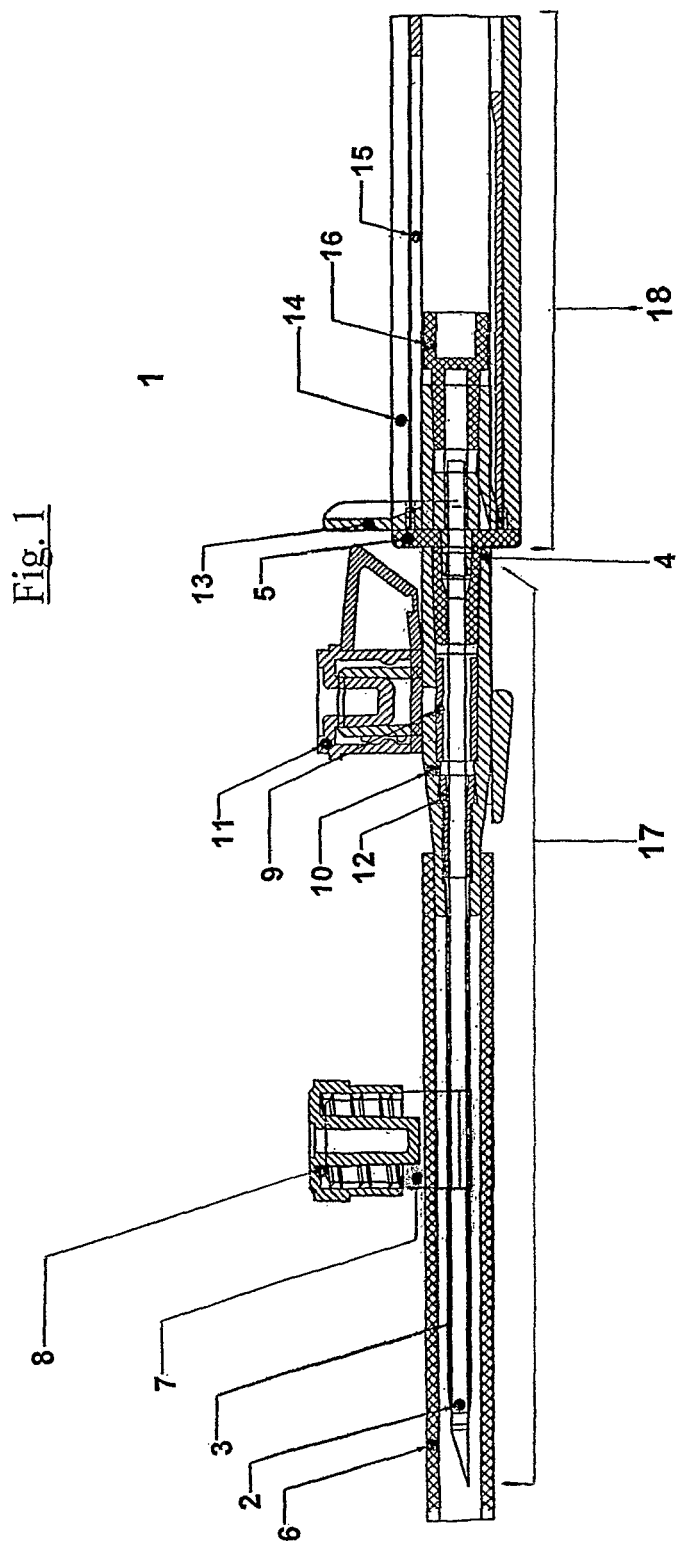
FIG. 1 is a diagrammatic representation of the intravenous cannulation or catheter insertion device of the invention comprising cannula assembly and detachable safety transfer chamber assembly as one unit.

The present invention relates to a safety medical device called the safety catheter insertion device which eliminates the chances of needle stick injuries to para-medical staff and medical personnel during insertion and after insertion to patients or while disposing of the catheter insertion device after use. The device of the present invention also ensures that the safety catheter insertion device cannot be re-used with wrong intention.

In the prior art catheter insertion devices, there is always a risk of needle stick injury to para-medical staff during use, withdrawal or disposal. This increases the chances of accidental spread of infection. During improper disposal, the infected cannula assembly may increase the chances of spread of infection unknowingly. Moreover, the catheter insertion device can be re-used, in spite of the fact that every individual packing of the catheter insertion device cautions "DO NOT RE-USE THE PARTIAL OR COMPLETELY WITHDRAWN GUIDE NEEDLE".

In the present invention when the safety catheter insertion device is used on patients then during cannula assembly withdrawal, the guide needle hub is held and pulled back into the sleeves. The guide needle hub is locked with cannula assembly with a first click sound and further withdrawal pulls back cannula assembly from the main body of catheter insertion device. The second click sound confirms the complete withdrawal of cannula assembly. The cannula assembly is completely enclosed into the sleeve container, which restricts and completely eliminates the chances of guide needle stick injury to para-medical staff and the medical personnel. The possibility of re-cannulation is also completely negated in the present invention. During disposal, since the cannula assembly is completely enclosed in a safe container, it completely eliminates chances of any infection to para-medical staff and the medical personnel.

Important Components of the Present Invention are:

Guide needle: Specially designed guide needle is beveled, back cut ground and siliconised for smooth and painless puncture.

Needle Hub: It prevents destabilization and provides better grip and control during cannulation. It may have specific thumb radius for proper grip during insertion.

Needle cover: Protects the guide needle and catheter from contamination as well as from accidental damage.

Catheter: Most biocompatible or blood compatible material known to mankind P.T.F.E. (Poly Tetra Fluro Ethylene) is preferably used for catheter, which has lowest coefficient of friction and reduces the chances of thrombophelebitis and sticking to vascular walls.

P.T.F.E. catheter is specially tapered, beveled tip and siliconised. The improved tip deisgn minimizes the resistance during insertion.

Thin walled catheter allows maximum flow rate.

Optimum distance between guide needle bevel and catheter tip is maintained.

Catheter material can be F.E.P./P.U. or as per specific requirement of customer also.

Flash Back Chamber: Unique or vented hub for higher flow rate and quick easy confirmation of correct vascular access.

Avoids blood spillage.

Prevents formation of air bubbles.

Threaded Stopper: Each Catheter insertion device is provided with a threaded stopper for secure closure of the medication.

Blister Packing: Each Catheter insertion device is individually packed in rigid/flexible blister sealed with peel open type Medical Grade Paper or Tyvek to maintain the prescribed shelf life of the product for safe use.

Referring to the rawings, FIG. 1, illustrates the catheter insertion device (1) of the invention comprises a cannula assembly (17) and a detachable safety transfer chamber assembly (18) as one unit, showing the various components thereof as given below and indexed using reference numbers guide needle (2);

catheter (3);

catheter (3) attached to a catheter holder (12) at the distal end;

at least one attachment site (4) at the proximal end of cannula assembly (17);

the said catheter (3) is slidably coaxially mounted on the outer circumference of the said guide needle (2);

guide needle (2) is in fluid communication with the lumen of the device extending form the proximal to the distal end;

safety transfer chamber assembly (18);

safety transfer chamber assembly (18) fitted to the cannula assembly (17) at the said attachment site (4) through the front cap (5);

a replaceable needle cover (6) to cover the exposed portion of the cannula assembly (17);

the cover (6) is provided with a threaded stopper holder (7) to hold a threaded stopper (luer lock)(8);

cannula assembly (17) comprises a securable opening (9) extending from the main body (10) for injecting external fluids including drips and medicaments, which is closed using a replaceable port cap (11);

safety transfer chamber assembly (18) comprising in combination: a front cap (5) constructed so as at to fit in the attachment site (4);

a needle hub (13) attached to flash back chamber (16) of the guide needle (2) for holding and sliding/moving needle (2) along the length of the catheter insertion device (1);

an outer sleeve (14) telescopically and slidably mounted on an inner sleeve (15), wherein the said inner sleeve (15) is coaxially mounted around the guide needle (2);

said inner sleeve (15) having lugs at one end; the said outer sleeve (14) extending from said front cap (5) at one end and having indentations complementary to the lugs of inner sleeve (15) at the other end for irreversibly locking the safety transfer chamber assembly (18) along with the retracted needle (2).

Figure 2:
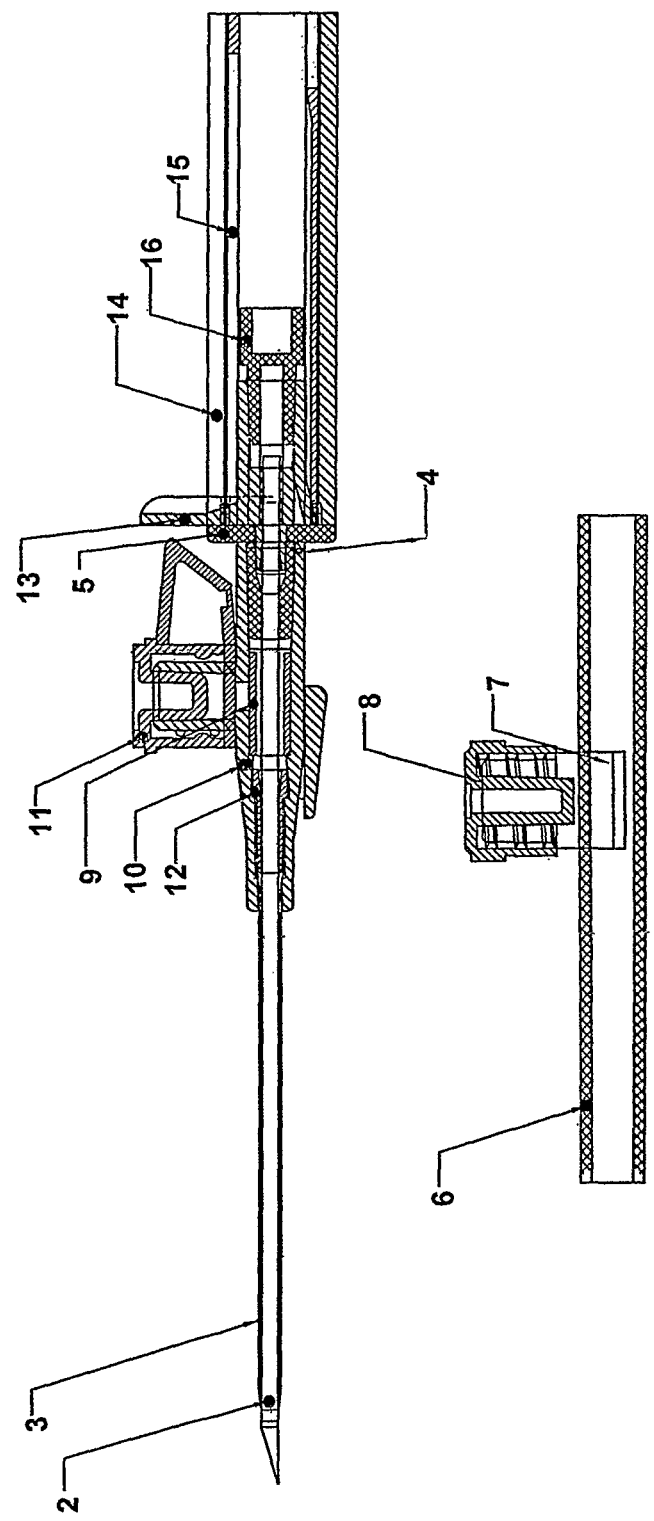
FIG. 2 is a diagrammatic representation of an uncapped catheter insertion device.

FIG. 2 is a diagrammatic representation of an uncapped catheter insertion device (1). FIG. 2 shows various components of the catheter insertion device (1) when the cover (6) is removed and the catheter (3) with needle (2) within is exposed.

Figure 3:
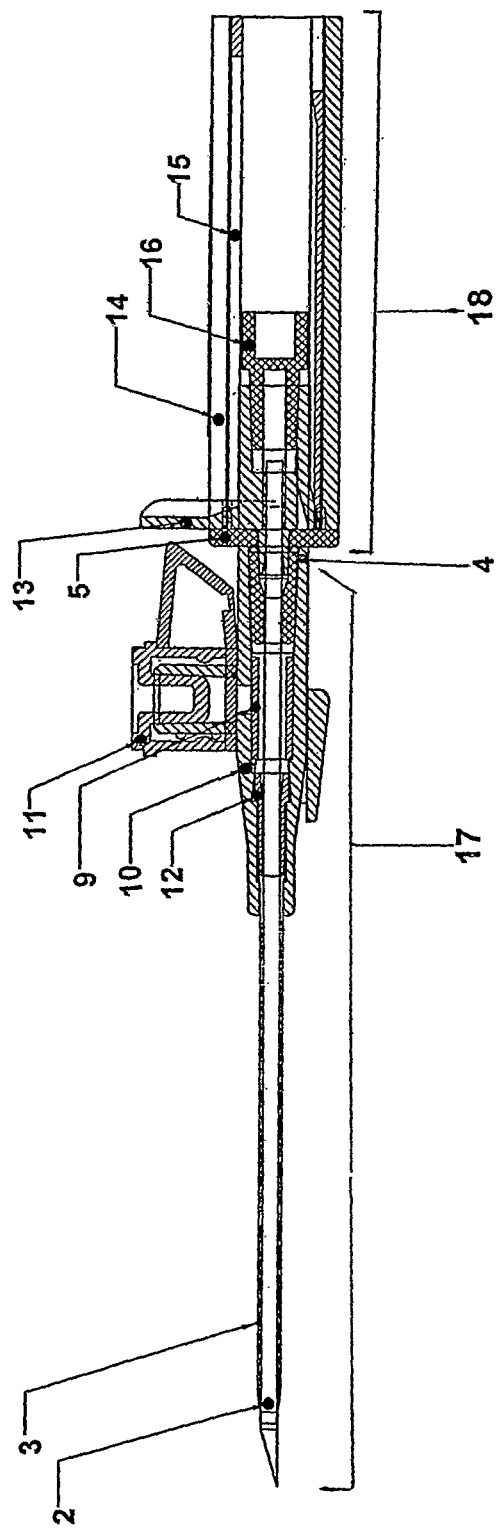
FIG. 3 is a diagrammatic representation of an uncapped catheter insertion device of FIG. 2 in a state to be inserted into a desired locus.

FIG. 3 is a diagrammatic representation of an uncapped catheter insertion device (1) of FIG. 2 in a ready to use condition, i.e. in a state when it can be inserted into a desired locus.

Figure 4:
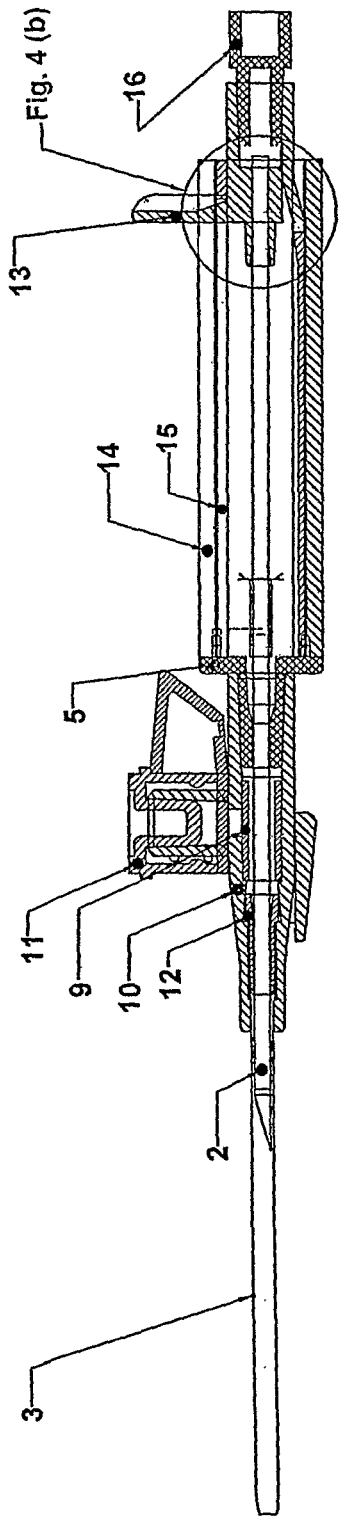
FIG. 4 is a schematic representation of the catheter insertion device in first half-lock stage, showing how the device is locked by a first-click sound when the guide needle is withdrawn form the locus after confirming blood in flash back chamber.
Figure 4:
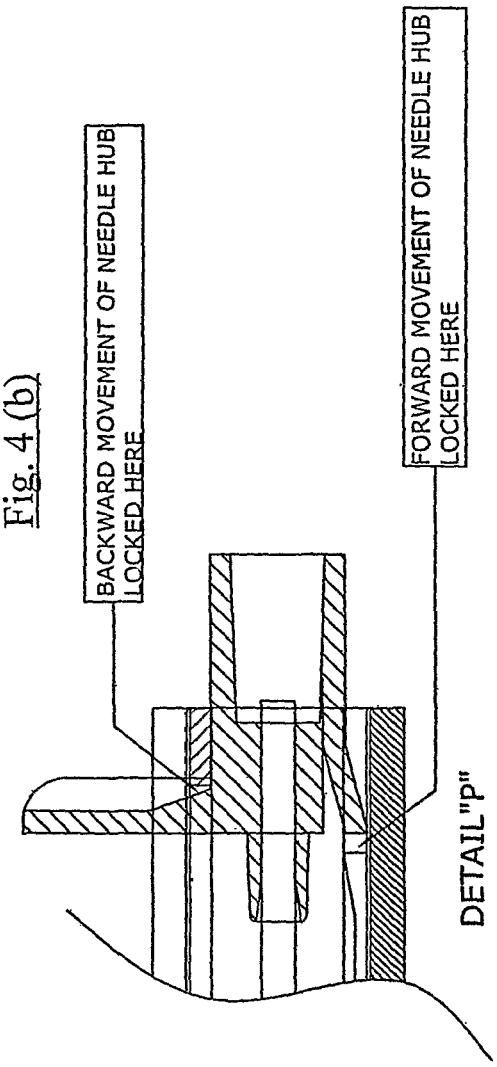

FIG. 4(*a*) is a schematic representation of the catheter insertion device (1) in half-lock stage, showing how the device is locked when the guide needle is withdrawn from the locus after confirming blood in flash back chamber. The first half-lock is confirmed by a light first-click sound. The first lock condition is schematically illustrated by the 'Detail "P"' diagram shown as FIG. 4(*b*). FIG. 4(*b*) further elucidates how backward and forward movements of needle hub are irreversibly locked by the first half-lock.

Figure 5:
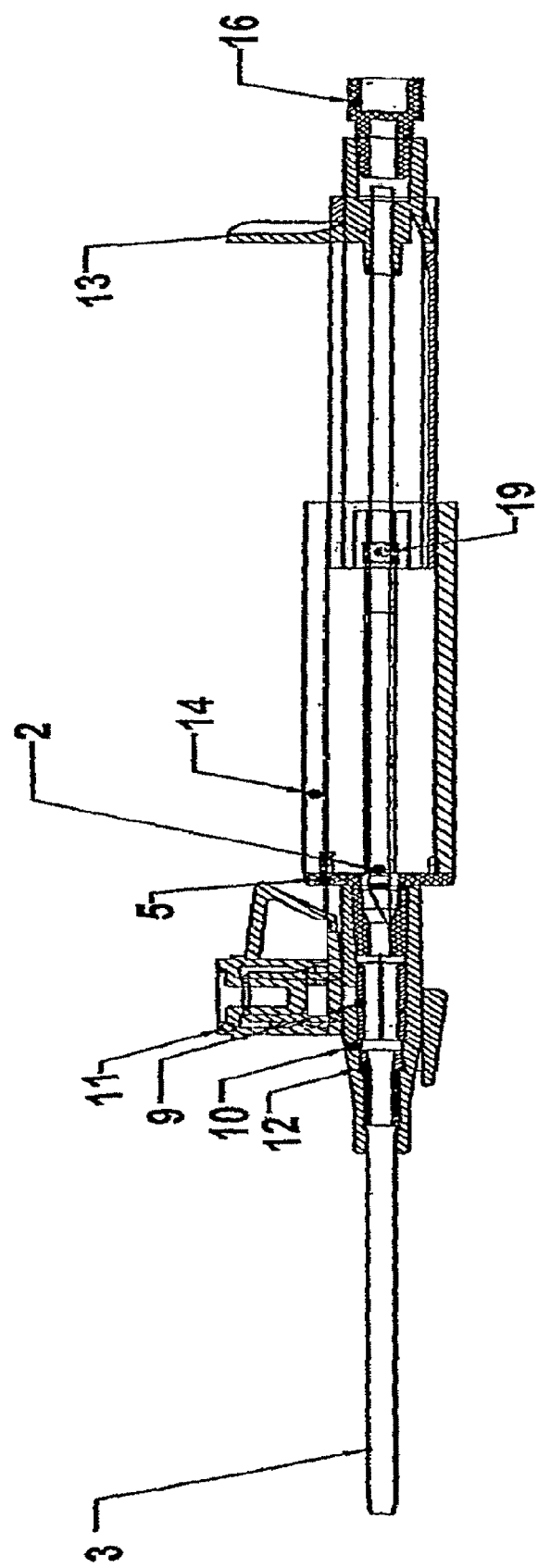
FIG. 5 is a schematic representation showing the catheter insertion device in full-lock stage, showing how the device is irreversibly locked by a second-click sound when the needle hub is pulled backward so that inner sleeve starts sliding in outer sleeve till it locks with the click sound.

FIG. 5 is a schematic representation showing the catheter insertion device (1) in full-lock stage, showing how the device is irreversibly locked by a second-click sound when the needle hub is pulled backward so that inner sleeve (15) starts sliding in outer sleeve (14) till it locks with the click sound.

FIG. 6 is a diagrammatic representation of the retracted needle locked in the safety chamber assembly (18) detached from the cannula assembly (17). It illustrates how the tip of the retracted needle is safely locked in the front cap (5) of the detached safety transfer chamber assembly (18).

In use, the site of the site of cannulation is cleaned in accordance with conventional medical procedures and the site, i.e., the vein where cannula is to be inserted is located. The needle cover (6) is removed and the needle (2) along with the external cannula (3) is fully inserted into the site, for e.g., the vein. Once the cannula is inserted in the vein, blood is drawn into the flashback chamber (16) confirming proper insertion of the cannula. The needle (2) is then slowly withdrawn from the cannula (3) until it is completely withdrawn from the cannula (3) with the cannula (3) retained completely inside the vein.

The safety transfer chamber assembly (18) is detachably connected to the cannula assembly (17) at the said attachment site (4). The safety transfer chamber assembly (18) consists of an outer sleeve (14) slidably mounted around an inner sleeve (15). The needle hub (13) is connected to or integral with said inner sleeve (15). The needle hub (13) and said inner sleeve (15) are equipped with first complementary interlocking mechanism (P) (FIGS. 4(*a*) and 4(*b*)) such that retracting the needle (2) from the catheter (3) locks the needle hub (13) with the inner sleeve (15) in a first locking position thereby preventing forward movement of the needle (2) and reinsertion of thereof in the catheter (3). Further retraction of the needle hub (13) causes the inner sleeve (15) to retract with it in said outer sleeve (14). As shown in FIG. 5, the inner and outer sleeves (15, 14) are equipped with a second complementary locking mechanism (19) such that in a fully retracted position of said inner sleeve (15) inside aid outer sleeve (14), the needle (2) is completely enclosed within the safety transfer chamber (18) and said inner sleeve (15) locks with the outer sleeve (14) at a second locking position, thereby preventing further axial or rotational movement of the two sleeves with respect to each other such that reuse of the needle (2) is completely prevented.

At this position, a gentle twist of the safety transfer chamber or assembly (18) to about 30° in either clockwise or counter clockwise direction detaches the safety transfer chamber (18) from the catheter assembly (17) as shown in FIG. 6. In this position, the safety transfer chamber with the used needle (2) safely and completely enclosed therewithin is ready for disposal with no risk of accidental injury to any person.

In a preferred embodiment, the first locking mechanism comprises at least a pair of lugs at the forward end of the needle hub, which snap fit into complimentary indentations on the inner sleeve.

In a preferred embodiment, the second locking mechanism comprises at least a pair of lugs at one end of the inner sleeve, which snap fit into complimentary indentations on the outer sleeve.

The inner sleeve (15) may preferably be tubular, semi tubular in the form of a tray with U-shaped cross section or may simply comprise of a base with two upstanding and opposing columns, said columns being two upright sections of a cylindrical tube, axially mounted around the guide needle. Such constructions of the inner sleeve provides a springy or biasing force to the inner sleeve which enable it to lock and snap fit with the outer sleeve at its side walls in a second locking position.

In a preferred feature, the said cannula assembly has a securable opening extending from its main body, which is used for injecting any additional medicine or fluid such as glucose, saline drip etc. When not in use, the opening is closed using a replaceable port cap (11).

In another preferred feature, catheter assembly is shielded/covered by a removable/replaceable protective cover (6). The removable/replaceable cover (6) is provided with a remvovable threadded stopper holder (7) to hold a threaded stopper (luer lock) (8). When the safety transfer chamber (18) is detached from the catheter assembly (17), the rear end of the catheter assembly, i.e., the attachment site (4) is shut using the threaded stopper/luer lock (8).

Advantages of the Invention

The present invention provides a safe and disposable device, which prevents the paramedical staff and the personnel involved from infection and diseases. This device provides for better grip and control during cannulation and may optionally have special thumb radius for proper grip during insertion. The device is provided with stainless steel needle, which is beveled, back cut ground and siliconised for smooth and painless puncture. Its improved tip design minimizes the resistance during insertion. Thin walled catheter allow maximum flow rate and prevents blood spillage formation of air bubbles.

We claim:

1. A catheter insertion device which comprises in combination:
   a cannula assembly having a catheter detachably attached to a catheter holder at the distal end and at least one attachment site at the proximal end, and having a lumen extending from the distal end to the proximal end;
   a guide needle mounted on a needle hub attached to a flash back chamber of the guide needle for positioning the cannula assembly to an operative position and sliding or moving the guide needle, wherein the catheter is slidably coaxially mounted on the outer circumference of the guide needle wherein the guide needle is in fluid communication with the lumen;
   a safety transfer chamber assembly detachably connected to the cannula assembly at the attachment site through a front cap, wherein the safety transfer chamber assembly comprises an outer sleeve slidably mounted around an inner sleeve, the needle hub projecting radially outward of the inner and outer sleeves to facilitate gripping thereof and cooperating with the inner sleeve to form a first complementary interlocking mechanism (P) at a first locking position wherein, upon retracting the guide needle from the catheter, the needle hub interacts with the inner sleeve to prevent forward movement of the guide needle and reinsertion thereof in the catheter, further retraction of the needle hub causing the inner sleeve to retract within the outer sleeve, the inner and outer sleeves being equipped with a second complementary interlocking mechanism such that in a fully retracted position of the inner sleeve, the guide needle is completely enclosed within the inner sleeve and the outer sleeve of the safety transfer chamber assembly and the inner sleeve locks with the outer sleeve at a second locking position, thereby preventing further axial or rotational movement of the two sleeves with respect to each other such that reuse of the guide needle is completely prevented.

2. The device as claimed in claim 1, wherein the first complementary interlocking mechanism (P) comprises at least a pair of lugs at the forward end of the needle hub, which snap fit into complementary indentations on the inner sleeve.

3. The device as claimed in claim 1, wherein the second complementary interlocking mechanism comprises at least a pair of lugs at one end of the inner sleeve, which snap fit into complementary indentations on the outer sleeve.

4. The device as claimed in claim 1, wherein the inner sleeve is tubular, semi tubular, or in the form of a tray with a U-shaped cross section.

5. The device as claimed in claim 1, wherein the inner sleeve comprises a base with two upstanding and opposing columns, the columns being two upright sections of a cylindrical tube, axially mounted around the guide needle.

6. The device as claimed in claim 1, wherein the cannula assembly has a securable opening extending from a main body of the cannula assembly, which is closed using a replaceable port cap.

7. The device as claimed in any claim 1, wherein the guide needle is movable to a retracted position through the proximal end of the cannula assembly for removal therefrom and is irreversibly locked inside the safety transfer chamber assembly.

8. The device as claimed in claim 1, wherein the guide needle is shielded or covered by a removable or replaceable protective cover.

9. The device as claimed in claim 8, wherein the removable or replaceable cover is provided with a threaded holder to hold a threaded stopper (luer lock).

10. The device as claimed in claim 1, wherein the guide needle is a hypodermic needle.

11. The device as claimed claim 1, wherein the catheter body is protected by a needle protection cover.

12. A safety transfer chamber assembly for use with an intravenous cannulation device having a guide needle, for safely locking in the guide needle after use to prevent reuse or contact with a user, the safety transfer chamber assembly comprising:

a needle hub for holding and slidably retracting the guide needle;

an outer sleeve slidably mounted around an inner sleeve, the guide needle being connected to or integral with the inner sleeve, the needle hub projecting radially outward of the inner and outer sleeves to facilitate gripping thereof and cooperating with the inner sleeve to form a first complementary interlocking mechanism (P) at a first locking position wherein, upon retracting the guide needle from the catheter, the needle hub interacts with the inner sleeve to prevent forward movement of the guide needle and reinsertion thereof in the catheter, the inner and outer sleeves being equipped with a second complementary locking mechanism such that in the fully retracted positions of the inner sleeve, the inner sleeve locks with the outer sleeve and the guide needle is completely enclosed within the inner sleeve and the outer sleeve of the safety transfer chamber assembly, and thereby preventing further axial or rotational movement of the two sleeves with respect to each other such that reuse of the needle is completely prevented.

13. A cannula assembly having a distal end for detachable attachment to a catheter holder and a proximal end with at least one attachment site, the cannula assembly having a lumen extending from the distal end to the proximal end;

a guide needle mounted on a needle hub attached to a flash back chamber of the guide needle for positioning the cannula assembly to an operative position and sliding or moving the guide needle, wherein the guide needle is in fluid communication with the lumen;

a safety transfer chamber assembly detachably connected to the cannula assembly at the at least one attachment site through a front cap, wherein the safety transfer chamber assembly comprises an outer sleeve slidably mounted around an inner sleeve, the needle hub being connected to or integral with the inner sleeve, the needle hub projecting radially outward of the inner and outer sleeves to facilitate gripping thereof and cooperating with the inner sleeve to form a first complementary interlocking mechanism (P) at a first locking position wherein, upon retracting the guide needle from the catheter, the needle hub interacts with the inner sleeve to prevent forward movement of the guide needle and reinsertion thereof in the catheter, further retraction of the needle hub causing the inner sleeve to retract with the needle hub in the outer sleeve, the inner and outer sleeves being equipped with a second complementary locking mechanism such that in a fully retracted position of the inner sleeve, the guide needle is completely enclosed within the inner sleeve and the outer sleeve of the safety transfer chamber assembly and the inner sleeve locks with the outer sleeve at a second locking position, thereby preventing further axial or rotational movement of the two sleeves with respect to each other such that reuse of the needle is completely prevented.

14. The cannula assembly as claimed in claim 13, wherein the guide needle is beveled, back cut ground and siliconised for smooth and painless venipuncture.

15. The cannula assembly as claimed in claim 13, wherein the guide needle is a hypodermic needle.

* * * * *